(12) United States Patent
Parker et al.

(10) Patent No.: US 8,738,113 B2
(45) Date of Patent: May 27, 2014

(54) RETROSPECTIVELY CORRELATED TURBO SPIN ECHO IMAGING

(75) Inventors: Dennis L. Parker, Centerville, UT (US); Jason K. Mendes, Draper, UT (US); Jordan Hulet, South Jordan, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 392 days.

(21) Appl. No.: 12/895,533

(22) Filed: Sep. 30, 2010

(65) Prior Publication Data

US 2012/0083687 A1 Apr. 5, 2012

(51) Int. Cl.
*A61B 5/055* (2006.01)

(52) U.S. Cl.
USPC ........................................................ 600/413

(58) Field of Classification Search
USPC ........................................................ 600/413
See application file for complete search history.

(56) References Cited

U.S. PATENT DOCUMENTS

| | | | |
|---|---|---|---|
| 4,855,910 A * | 8/1989 | Bohning | 324/309 |
| 5,133,357 A | 7/1992 | Dumoulin et al. | |
| 5,320,099 A | 6/1994 | Roberts et al. | |
| 5,329,925 A | 7/1994 | NessAiver | |
| 5,348,011 A | 9/1994 | NessAiver | |
| 5,417,214 A | 5/1995 | Roberts et al. | |
| 5,447,155 A | 9/1995 | NessAiver | |
| 5,521,502 A | 5/1996 | Siegel, Jr. et al. | |
| 5,694,935 A | 12/1997 | Damadian | |
| 5,713,358 A | 2/1998 | Mistretta et al. | |
| 5,830,143 A | 11/1998 | Mistretta et al. | |
| 5,865,747 A | 2/1999 | Steckner | |
| 5,873,825 A | 2/1999 | Mistretta et al. | |
| 5,881,728 A | 3/1999 | Mistretta et al. | |
| 6,076,004 A | 6/2000 | Kanayama et al. | |
| 6,240,310 B1 | 5/2001 | Bundy et al. | |
| 6,377,832 B1 | 4/2002 | Bergman et al. | |
| 6,408,201 B1 | 6/2002 | Foo et al. | |
| 6,408,202 B1 | 6/2002 | Lima et al. | |
| 6,434,412 B1 | 8/2002 | Simonetti et al. | |
| 6,492,811 B1 | 12/2002 | Foxall | |
| 6,516,210 B1 * | 2/2003 | Foxall | 600/410 |
| 6,693,768 B1 | 2/2004 | Crue et al. | |
| 6,781,375 B2 | 8/2004 | Miyazaki et al. | |
| 6,794,867 B1 | 9/2004 | Block et al. | |
| 6,801,800 B2 | 10/2004 | Miyazaki et al. | |
| 7,199,582 B2 | 4/2007 | Keegan et al. | |
| 7,209,777 B2 | 4/2007 | Saranathan et al. | |
| 7,253,620 B1 | 8/2007 | Derbyshire et al. | |
| 7,372,266 B2 | 5/2008 | Markl et al. | |

(Continued)

OTHER PUBLICATIONS

Anderson et al., "Gaussian Binning: a new kernel-based method for processing NMR spectroscopic data for metabolomics", Metabolomics, 4:261-272, published Aug. 20, 2008.*

(Continued)

*Primary Examiner* — Jonathan Cwern
(74) *Attorney, Agent, or Firm* — Peter R. Withstandley (57) ABSTRACT

Systems and methods which generate a sequence of images using turbo spin echo magnetic resonance imaging which are retrospectively correlated with periodic motion occurring within a subject being imaged are described. In one embodiment, k-space measurements (or the measurements from which images are formed) are captured during, and correlated with, different phases in a cardiac cycle of the subject. With this sequence, the images that are produced are able to show, and/or compensate for, motion correlated with the cardiac cycle of the subject.

11 Claims, 9 Drawing Sheets

(56) References Cited

U.S. PATENT DOCUMENTS

| | | | |
|---|---|---|---|
| 8,099,148 B2 * | 1/2012 | Madore | 600/410 |
| 2002/0095085 A1 | 7/2002 | Saranathan et al. | |
| 2003/0050554 A1 * | 3/2003 | Schaffer | 600/410 |
| 2005/0245812 A1 | 11/2005 | Kim et al. | |
| 2006/0013458 A1 | 1/2006 | Debbins et al. | |
| 2006/0125476 A1 | 6/2006 | Markl et al. | |
| 2008/0298661 A1 * | 12/2008 | Huang | 382/131 |

OTHER PUBLICATIONS

Web page http://www.revisemri.corniquestions/pulse_sequencesitse, "Turbo Spin Echo", printed on Mar. 20, 2013.

* cited by examiner

RETROSPECTIVELY CORRELATED TURBO SPIN ECHO IMAGING

GOVERNMENT INTERESTS

This invention was made with government support under Grants HL048223 and HL057990, awarded by the National Institutes of Health. The government has certain rights in the invention.

TECHNICAL FIELD

The disclosure relates generally to magnetic resonance imaging and, more particularly, to reconstructing images with motion correlation data to analyze internal motion of a subject.

BACKGROUND OF THE INVENTION

There is evidence that carotid artery imaging techniques can be used to detect disease and classify subjects that will benefit from interventions. Because Magnetic Resonance Imaging (MRI) can acquire images with a variety of different tissue contrasts, it presents an advance over x-ray techniques in the ability to discriminate between different types of soft tissue and the potential to discriminate between important atherosclerotic plaque components. Turbo spin echo (TSE) MRI pulse sequences, with efficient acquisition of T1, T2 and proton density weighted images have become very useful in the evaluation of cervical carotid artery disease. Current high-resolution three-dimensional (3D) TSE techniques could also be valuable in carotid MRI. However, motion artifacts that arise due to the relatively long data-acquisition time of current TSE pulse sequence methods result in an unacceptably high fraction of non-interpretable images. As a result, TSE techniques result in obvious blurring or ghosting artifacts that greatly reduce the quality of the images.

Methods can be implemented to reduce artifacts caused by poor acquisition time. For example, applying parallel imaging techniques may be used to reduce acquisition time and thereby reduce the likelihood of motion artifacts. Parallel imaging techniques can also be used to compensate for artifacts due to swallowing and other neck muscle movements. Reduced field of view sequences with more efficient double inversion blood suppression have also shown reduced susceptibility to these types of motion artifacts. Single shot sequences such as Half Fourier Acquisition Single shot Turbo spin Echo (HASTE) can also be used to reduce acquisition time and hence the susceptibility to certain motion artifacts. Navigators and dedicated motion detection RF coils have been shown to be successful in detecting and rejecting data corrupted by swallowing. Additionally, using average specific phase encoding ordering or comparing adjacent sets of k-space data lines are alternative methods for detecting data corrupted by patient motion.

Other MRI scanning methods, such as Gradient Echo (GRE) methods, are used for faster imaging to reduce more complex motion artifacts, such as ones that are caused by the movements of the cardiac cycle. These may include synchronizing data acquisition with the heart cycle to insure controlled capture across all data points. GRE-based pulse sequences can have a very short Repetition Time (TR) (<30 ms) and can therefore be efficiently designed as cine sequences to obtain complete image measurements at multiple cardiac phases in the same acquisition. Pulse sequences such as cine-GRE or cine-Phase-Contrast (PC) have been used to show carotid artery motion and cyclic blood flow. However, gradient echo techniques are limited in their ability to create acceptable images of soft tissue due to the above noted short TR time and typically worse signal-to-noise ratio performance.

TSE techniques, on the other hand, generate detailed images of soft tissue. However, the same methods to compensate for motion artifacts that are caused by the movements of the cardiac cycle are not used with TSE techniques. This is in part because of the relatively long TR required by TSE techniques (>500 ms). Acquisitions synchronized with the heart cycle which use TSE techniques typically only obtain one image at a single cardiac phase. Accordingly, synchronized acquisitions using TSE techniques are generally only used to reduce the effect of cardiac motion by acquiring data at a point during a specific time period of the cardiac cycle, e.g., a point during the diastole period. Further, synchronization lengthens the acquisition time due to the need to acquire multiple scans at each specific point in the cardiac cycle. This additional time results in increased susceptibility to swallowing and respiratory motion artifacts. Because of this, synchronized acquisitions are rarely used in a TSE environment. This problem can be improved somewhat by limiting gating to just the central portion of k-space, however, the effect of a variable TR on the resulting image is still unacceptable.

BRIEF SUMMARY OF THE INVENTION

Embodiments described herein introduce systems and methods which generate a sequence of images using turbo spin echo magnetic resonance imaging which are retrospectively correlated with periodic motion occurring within a subject being imaged. In one embodiment, k-space measurements (or the measurements from which images are formed) are captured during, and correlated with, different phases in a cardiac cycle of the subject. With this sequence, the images that are produced are able to show, and/or compensate for, motion correlated with the cardiac cycle of the subject.

In one embodiment, a method is provided which converts a conventional multislice, single image per slice, TSE acquisition into a multislice, retrospectively heart cycle correlated image sequence per slice, TSE acquisition (such correlated TSE acquisitions are referred to herein as a cineTSE). Because the cineTSE images are correlated with a subject's heart cycle, embodiments are able to reduce artifacts caused by pulsatile motion. Embodiments may utilize the cineTSE sequence to generate a full sequence of heart cycle correlated images throughout the cardiac cycle at each slice location in the same amount of acquisition time that is conventionally used by standard (or gated) TSE sequences to produce a single image at each slice location.

Embodiments of the described cineTSE sequence may be implemented using the same acquisition time of a standard two average TSE sequence. As a result, embodiments may avoid non-constant TR effects which are typically associated with gated sequences, such as ghosting in high contrast tissue areas. Additionally, in some embodiments the TSE acquisition may be obtained asynchronously with the cardiac cycle which will result in the images not suffering from problems caused by non-constant TR periods.

In some embodiments, additional processing methods may be applied to a captured sequence of measurements from which the images are formed to complete image reconstruction. One method may utilize information from multiple receiver Radio Frequency (RF) coils of the MRI device to implement parallel imaging methods. Another method may include a constrained reconstruction method where an a priori constraint is applied which assumes an object is not going to change very rapidly from one image bin to the next image bin.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which.

DETAILED DESCRIPTION OF THE INVENTION

In portions of the following description, embodiments are illustrated in terms of imaging a human subject and monitoring cardiac cycle movements. However, it is noted that the inventive aspects discussed herein may be used when imaging any type of subjects while monitoring any form of periodic movement therein. The specific examples are utilized for descriptive purposes only and are not intended to be limiting. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 1:
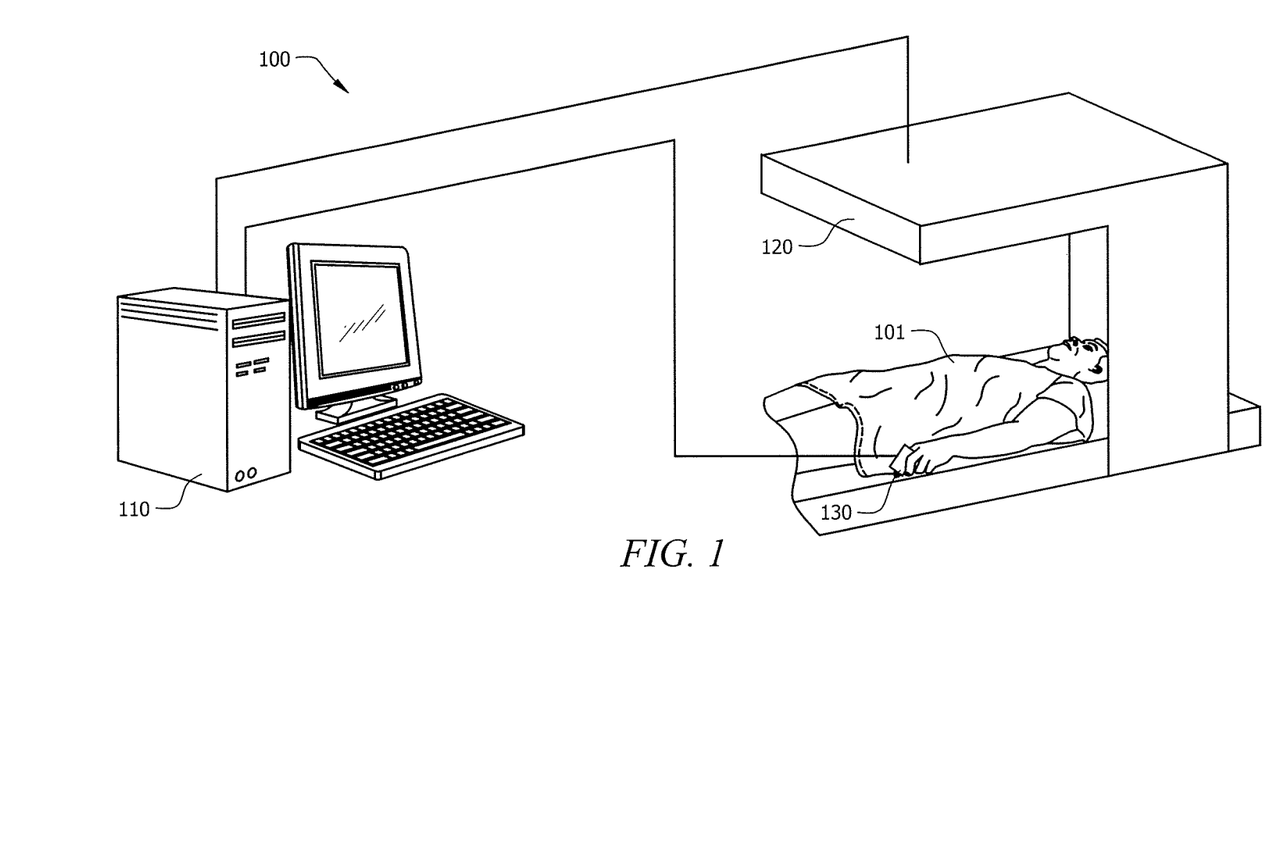
FIG. 1 illustrates an imaging system in accordance with an embodiment of the present application.

Directing attention to FIG. 1, an imaging system adapted according to an embodiment of the present invention is shown as imaging system 100. Imaging system 100 comprises processor based system 110 operatively coupled to transducer 120 and periodic signal monitor 130, for use in collecting imaging data with respect to subject 101. Subject 101 may comprise a patient for which imaging of a portion of the patient's body is desired. Such imaging as provided by imaging system 100 may comprise reconstruction of images of internal body structure (e.g., organs, cavities, bones, etc.) using, for example, TSE MRI techniques.

Periodic signal monitor 130 may be a cardiac cycle monitor and implemented using any method which can provide timing information of the cardiac cycle. Periodic signal monitor 130 is shown as a finger-connected pulse oximeter. Such a pulse oximeter functions to measure pulsation of the blood in the finger and the pulsation is closely synchronized with the beating of the heart. However, there is a small time delay between the compression of the heart and the actual pulse of the blood in the finger which may be accounted for, if desired. For example, one method of accounting for this delay may include adjusting the periodic signal phase when correlating a cardiac cycle with acquired images. It is noted that other methods of cardiac monitoring may be used. For example, a pressure sensor which reads a pressure pulse may be placed on the on the neck of a subject, ECG leads may be placed on a subject, etc. Periodic signal monitor 130 may also be sensors calibrated to measure other types of periodic motions such as breathing periods, and the like.

Processor based system 110 of embodiments comprises a processor (e.g., central processing unit (CPU), application specific integrated circuit (ASIC), etc.), memory (e.g., random access memory (RAM), read only memory (ROM), disk memory, optical memory, etc.), and appropriate input/output (I/O) apparatus (e.g., display, pointing device, keyboard, printer, speaker, microphone, etc.) operable under control of an instruction set (e.g., software, firmware, etc.) defining operation as described herein. Such operation may provide image reconstruction corresponding to the configuration of transducer 120 and periodic signal monitor 130.

Figure 2:
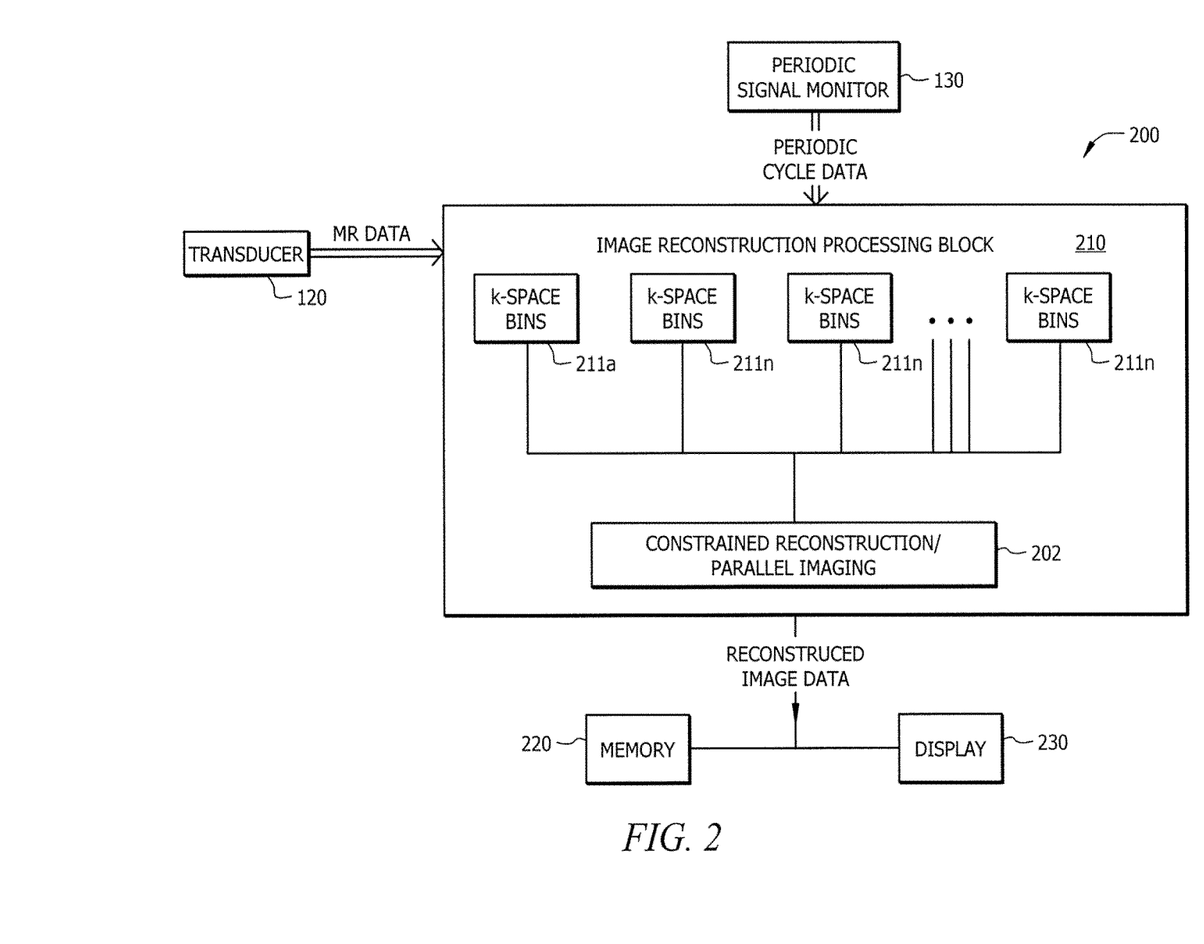
FIG. 2 illustrates an image reconstruction framework in accordance with an embodiment of the present application.

Imaging system 100 of the embodiment is adapted to utilize cineTSE acquisition techniques described herein to reconstruct images. An image reconstruction framework providing cineTSE acquisition techniques as may be utilized by imaging system 100 is shown in FIG. 2 as image reconstruction framework 200. Image reconstruction framework 200 may be implemented, at least in part, as instructions operable upon the processor of processor based system 110 of imaging system 100.

Image reconstruction framework 200 of the illustrated embodiment may receive raw Magnetic Resonance (MR) data from transducer 120 corresponding to a TSE sequence, and cardiac cycle data from periodic signal monitor 130. This information is provided to image reconstruction processing module 210. In some embodiments, the turbo spin sequence may be a conventional sequence designed primarily for generating a simple static image. The sequence is correlated by processing module 210 with a simultaneous time measurement of a pressure pulse received from periodic signal monitor 130. The received MR data is then sorted into k-space bins 211a-n based upon their relative time in the cardiac cycle.

In some embodiments, the periodic signal received from periodic signal monitor 130 will be a sinusoidal wave. In these embodiments, bins 211a-n may be configured to represent time divisions of a single reference wave period of the sinusoid. MR data received from transducer 120 may be received across multiple periods of a periodic signal. Embodiments track where in the multiple periodic cycles the MR data is captured, and correlates the MR data with the time divisions of bins 211a-n that correspond to the location in the particular periodic cycle.

With the data in bins 211a-n, images are reconstructed that may depict and/or compensate for motion within the subject being imaged. In some embodiments, the data in bins 211a-n may create a sequence of non-reconstructed image data such as in the event that there is not enough data to reconstruct a complete image. This can occur due to the fact that, in some embodiments, the cardiac cycle is asynchronous with the image scanner, which will cause it to yield random image samples that may not contain complete information representing motion throughout the cardiac cycle.

When incomplete information is obtained, additional processing methods may be undertaken to complete image reconstruction at processing block 202. One additional method utilizes information from multiple RF coils in transducer 120, to implement parallel imaging methods. In parallel MR imaging, a reduced data set in the phase encoding direction(s) of k-space is acquired to shorten acquisition time, combining the signal of several coil arrays on a transducer. The spatial information related to the phased array coil elements is utilized for filling in missing information corresponding to empty bins.

Another method may be a constrained reconstruction method where an a priori constraint is applied that assumes that the object is not going to change very rapidly from one image bin to the next image bin. With the assumption that the changes in a given image will be relatively small with respect to a previous image, an iterative algorithm may be utilized that uses the data measured, along with these constraints, and converges on the set of images that satisfy the constraints and satisfy the measured data. Any method, such as discussed above, which is able to compensate for missing information in one or more of bins 211a-n may be utilized separately, or in combination in order to yield a sequence of images which accounts for the motion caused by the heart that is occurring asynchronously with the image acquisition.

Reconstructed image data is produced by image reconstruction processing block 210. This data may be stored to memory block 220. Memory block 220 may be included as part of processor based system 110, or may be located on an external memory device. Alternatively, the reconstructed image data may be output to a display device, such as display device 230.

In one embodiment, information about a subject's cardiac cycle is recorded during the MRI scan utilizing a pulse oximeter. The acquired k-space data lines are sorted into N, temporal bins, which may correspond to bins 211a-n, according to the time elapsed from a reference time point such as the last systolic trigger. The result is N, undersampled data bins, each representing a different phase of the cardiac cycle. The undersampled images are reconstructed by simultaneously considering information encoded by the coil sensitivities as well as applying a temporal constraint. This is accomplished according to embodiments by minimizing the following objective function:

$$G = \|W(k_x,k_y,t) \cdot \Im_{xy}[s_n(x,y) \cdot m(x,y,t)] - d_n(k_x,k_y,t)\|_2^2 + \|\lambda(x,y) \cdot \nabla_t[m(x,y,t)]\|_2^2 \quad (1)$$

where t is the time (bin) in the cardiac cycle, $W(k_x, k_y, t)$ is a weight function specifying which lines in k-space have been acquired in each bin, $\Im_{xy}()$ is the 2D Fourier transform along the spatial coordinates, $s_n(x,y)$ is the coil sensitivity of the $n^{th}$ coil, $d_n(k_x, k_y, t)$ is the actual data acquired from the $n^{th}$ coil in the bin, $\lambda(x,y)$ specifies the level of temporal constraint and $\nabla_t()$ is a temporal gradient. Since m(x,y,t) is periodic in time, the following definition of $\nabla_t()$ has been found to be optimal compared to methods that estimate the temporal gradient using only a few surrounding points in time.

$$\nabla_t[m(x, y, t)] = \Im_t^{-1}\left\{\Im_t[m(x, y, t)] \cdot \frac{2\pi i f}{N_t}\right\} \quad [2]$$

Equation [1] is minimized using the following gradient term:

$$\nabla_m G = -2\lambda^2 \nabla_t^2(m) = 2\sum_n s_n^* \cdot \Im_{xy}^{-1}\left[W \cdot \Im_{xy}(s_n m) - d_n\right] \quad [3]$$

The images are then reconstructed using a non-linear conjugate gradient descent algorithm in conjunction with the objective function in Equation [1] and the gradient term in Equation [3].

The following description of FIGS. 3-9C describes example implementations and results of embodiments of the present invention. The specific methods used in this example are described for illustrative purposes only to facilitate one of ordinary skill in the art in understanding the concepts described herein, and are not intended to limit the scope of the concepts. All data sets were obtained on a Siemens TIM Trio 3T MRI scanner with a modified Turbo Spin Echo (TSE) sequence. The modified sequence is different from a standard TSE sequence in that the MRI scanner also acquires and store the periodic motion information, e.g. from the pulse oximeter and that the density of line sampling in k-space may be changed according to FIG. 3.

Figure 3:
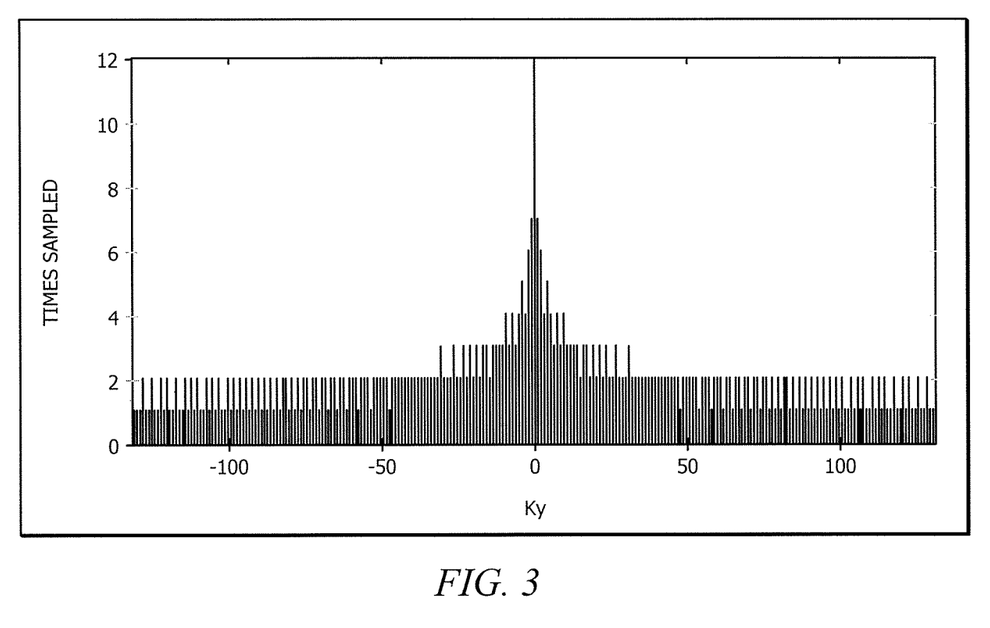
FIG. 3 shows a typical sampling density resulting from the cineTSE sequence utilized with embodiments of the present application.

In this cineTSE technique, the cardiac cycle is divided into a number of bins and each echo in each TSE echotrain is assigned to a bin based upon its time in the cardiac cycle. As discussed above, the received echo signals may originate across multiple periodic cycles. In these embodiments, the echoes are assigned based on their representative time of a reference period. Because readout of an echotrain can require over 100 ms (sometimes as much as 200 ms), it is not uncommon for the echoes in an echotrain to be assigned to two or more bins. To help ensure that each temporal data bin contains a sufficient number of lines near the center of k-space (where most of the image energy is found), the TSE sequence was modified to more frequently sample (slightly oversample) the center of k-space. To prevent an increase in scan time, this is accomplished at the cost of missing varying lines near the edge of k-space in each average. Every line of k-space is sampled at least once during the entire acquisition. FIG. 3 shows a typical sampling density resulting from the modified TSE sequence used in this study. In this case, 528 lines were sampled from a k-space spanning 264 lines. This corresponds to the same number of lines that would have been sampled with two full averages and a uniform sampling density.

Data used to generate images and plots in FIGS. 4A-6C and 8A-9C was acquired with a T2 weighted TSE sequence with a four channel neck coil, two averages, a resolution of 0.6 mm×0.6 mm×2 mm, twelve echoes per train and a TR/TE of 2.5 s/61 ms. The data used in FIGS. 7A-D was acquired with a T1 weighted TSE sequence with a sixteen channel neck coil, two averages, a resolution of 0.5 mm×0.5 mm×2 mm, twelve echoes per train and a TR/TE of 650 ms/8 ms.

In this particular study, a goal was to reconstruct the magnitude images. It was deemed sufficient to estimate the coil sensitivities as:

$$s_n(x, y) = \frac{m_n(x, y)}{\sqrt{\varepsilon + \sum_n m_n(x, y) m_n^*(x, y)}} \quad [4]$$

where $\varepsilon$ is a small constant and $m_n(x,y)$ is the image estimate from the $n^{th}$ coil. In cases where phase information from the final images is desired, a more specific measure of the coil sensitivities may be implemented.

Figure 4A:
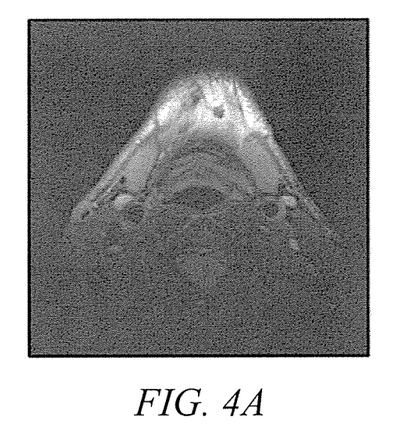
FIG. 4 illustrates a TSE data set with a corresponding spatially varying temporal constraint in accordance with an embodiment of the present application.
Figure 4B:
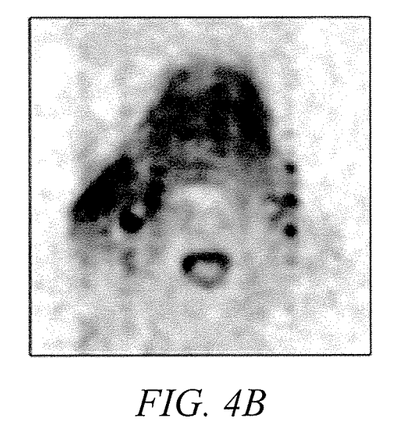

When correlating data to the cardiac cycle, some embodiments may constrain pixels varying with frequencies unrelated to the heart rate more strongly than those varying at frequencies near the heart rate. This was accomplished using the spatially varying temporal constraint of:

$$\lambda(x, y) = \sum_f \Im_t [m(x, y, t)] \cdot \alpha(f) \quad [5]$$

where $\alpha(f)$ is a bandpass filter selecting the frequency components occurring near the patient's average heart rate. In this study, $\lambda(x,y)$ is scaled to a range of zero (where pixels vary near the patients heart rate) to ~0.1 (where the pixel variations seem uncorrelated to the cardiac cycle). The acquired data, $d_n(k_x, k_y, t)$ is scaled so that our final image, $m(x,y,t)$, has a magnitude range of approximately 0~1.0. In addition, the temporal map may be constrained to be smooth by convolving the result of Equation [5] with a Gaussian (FWHM of ~8 pixels). A representative image slice and the corresponding temporal constraint are shown in FIGS. 4A and 4B. In FIG. 4, the standard TSE image shown in FIG. 4A along with $\lambda(x,y)$ (see Equation [6]) shown in FIG. 4B. The temporal constraint map of FIG. 4B is at a maximum in areas where pixel fluctuations have little correlation to the cardiac cycle and at a minimum in areas where the fluctuations correlate highly with the cardiac cycle. It is noted that this method of determining the spatial constraint can lead to blood pulsation artifacts being allowed. This is seen in the pulsatile artifact of the left carotid of FIG. 4B where the left carotid is replicated equally spaced vertically. Other methods may be utilized which force the constraint to be zero only at the true carotid and set the others to ~0.1 to obtain a more true reconstruction.

Since missing data lines are calculated using coil sensitivities and a temporal constraint, there may be a practical limit on the number of temporal bins into which the data should be sorted. Too few data bins might not allow enough temporal resolution to observe important events in the cardiac cycle. Too many bins and the data becomes too heavily temporally constrained and imposes a computational burden on the iterative reconstruction. In these experiments, it has been observed that sorting data into more than twelve temporal data bins, when two data averages have been acquired, does not yield significant improvements to the results. Therefore, unless specified, for purposes of this discussion all data is sorted into twelve temporal data bins. However, it is noted that the inventive concepts herein are not limited to any number of data bins.

Additionally, the cineTSE sequence may acquire data independent of the cardiac cycle and as a result some of the acquired data lines may occur on or near the boundary of the data bins. This data may reasonably be sorted into more than one temporal data bin. Such an effect can be taken into account by allowing our data bins to overlap slightly. In some cases, an overlap of 50% is utilized to help ensure each data bin contains an adequate amount of data but not too much to blur results in the temporal direction.

Finally, during the sorting process it is possible at times to sample a particular line of data in a given data bin multiple times. One way to include this effect is to allow $W(k_x, k_y)$ to assume values other than 0 or 1. Alternatively, we can average any line that is sampled more than once and keep the original definition of $W(k_x, k_y)$. It has been found that the averaging method yields similar results to the first but is less computationally demanding. As a result, any data line that is sampled multiple times in a particular bin is averaged.

Figure 5A:
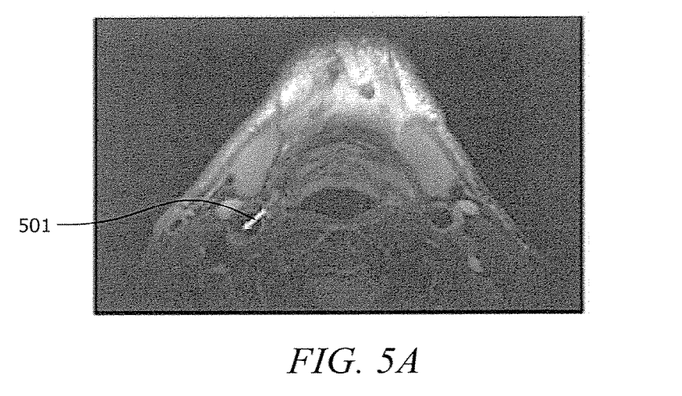
FIG. 5 illustrates results from flow artifact identification methods using a T2 weighted cineTSE reconstruction in accordance with an embodiment of the present application.
Figure 5B:
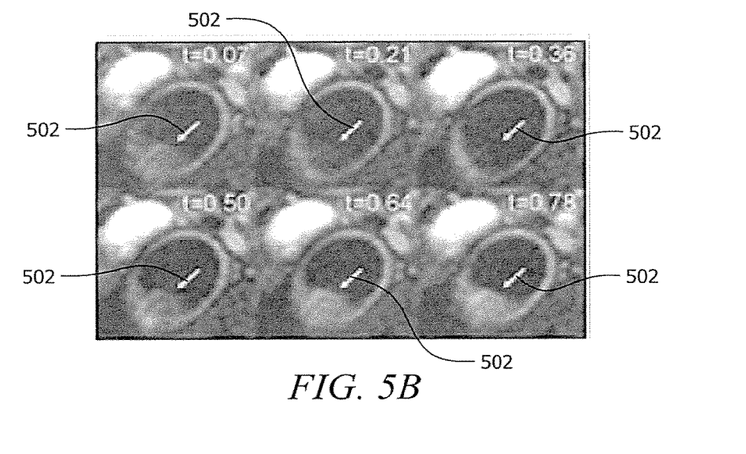
Figure 5C:
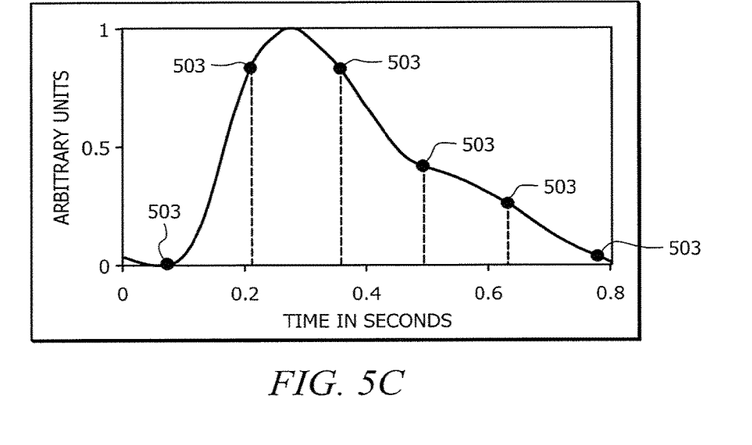

FIGS. 5A-C illustrate methods for flow artifact identification using a T2 weighted cineTSE reconstruction (four channel receive coil and two data averages). The standard TSE image, FIG. 5A, exhibits a flow artifact in the carotid artery, just below the bifurcation indicated by arrow 501, that is observed with this patient when the data is reconstructed in the standard way. It is noted that the arrows in FIGS. 5A-B, 7A-D and 8A are used to assist in indicating the relevant area of the figure, and are not part of the image. FIG. 5B shows six (of twelve total) images obtained from a cineTSE reconstruction. The six images are selected with equal spacing in the cardiac cycle at the times shown on the average pressure pulse in FIG. 5C. The flow artifact is seen to come and go throughout the cardiac cycle and can easily be identified in the cineTSE images at arrow 502. The time of each of the six images of FIG. 5B relative to the systolic trigger correspond to the time points 503 on the average pressure pulse wave form of FIG. 5C.

Figure 6A:
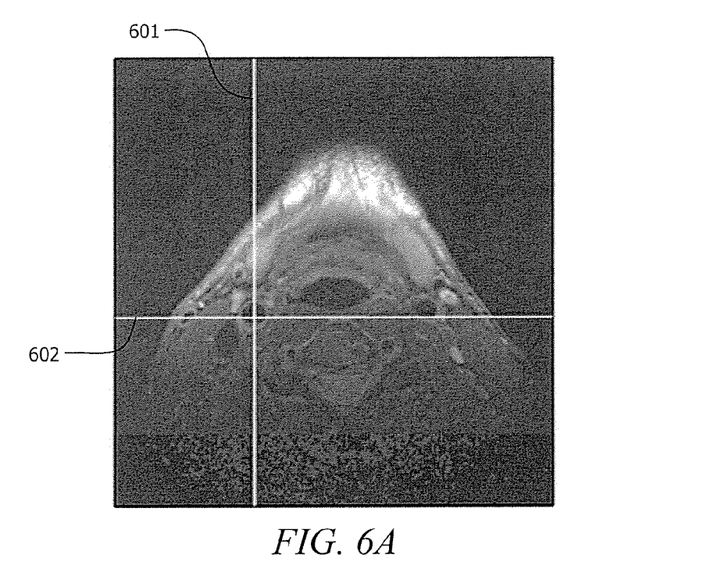
FIG. 6 illustrates the improvement of vessel wall depiction using a T2 weighted cineTSE in accordance with an embodiment of the present application.
Figure 6B:
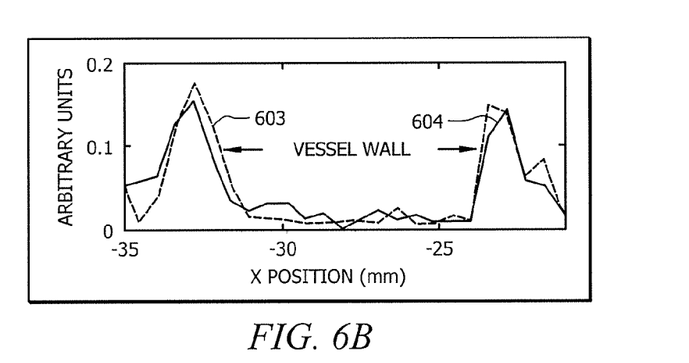
Figure 6C:
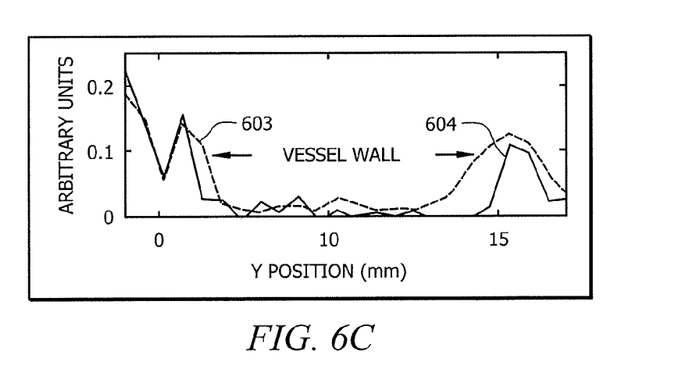

FIGS. 6A-C illustrates the improvement of vessel wall depiction using a T2 weighted cineTSE. Profiles through a carotid artery are observed in two orthogonal directions 601 and 602 of FIG. 6A. FIGS. 6B and 6C illustrate the profiles along the vertical (phase encode) 601 and horizontal (frequency encode) 602 directions, respectively. The dashed lines 603 in FIGS. 6B and 6C are the profiles measured when a standard TSE sequence (two averages) is used, while the solid lines 604 is the result obtained using a systolic image from the same data obtained using the cineTSE reconstruction. The discrepancy in vessel wall thickness is especially evident in the phase encode direction (FIG. 6C).

Figure 7A:
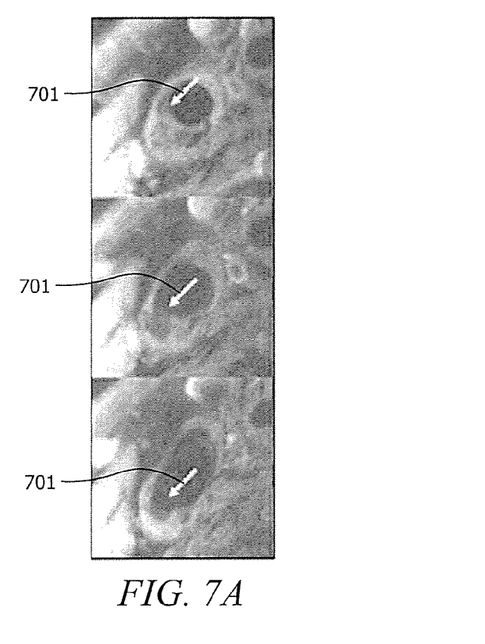
FIG. 7 illustrates T1 weighted cineTSE images from a patient with an ulceration of plaque in their carotid artery in accordance with an embodiment of the present application.
Figure 7B:
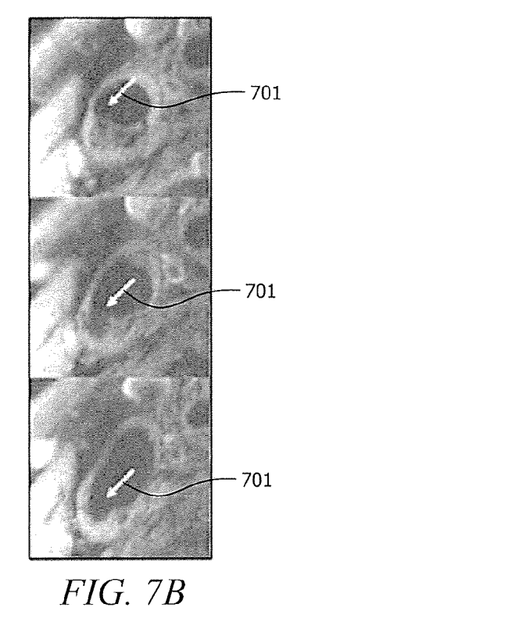
Figure 7C:
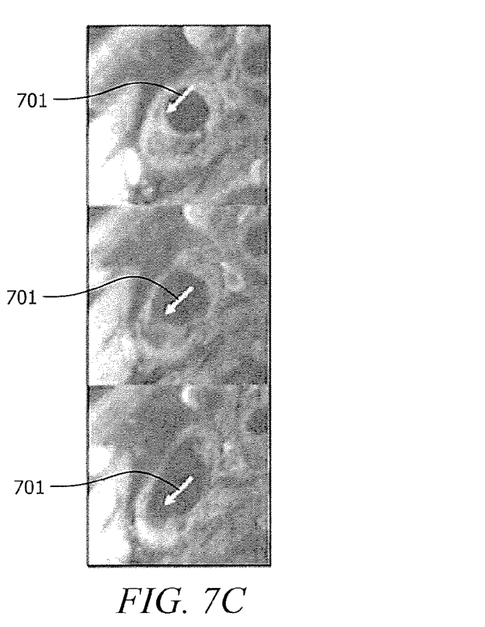
Figure 7D:
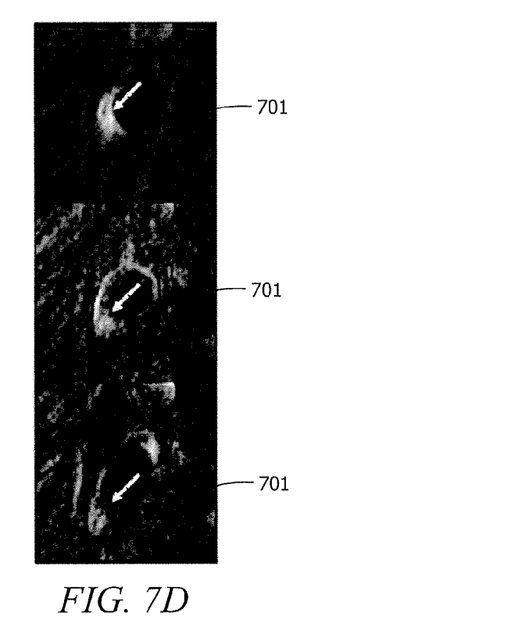

FIGS. 7A-D illustrate T1 weighted cineTSE images from a patient with an ulceration of plaque in their carotid artery. Each column contains images from the same three consecutive slices. FIG. 7A contains the standard TSE images (two averages), FIGS. 7B and 7C show images reconstructed in the systolic and diastolic phases, respectively, with FIG. 7D showing the signal difference between the two cardiac phases. Arrows 701 on each slice indicate areas where flow artifact might obscure the true nature of the plaque.

Figure 8A:
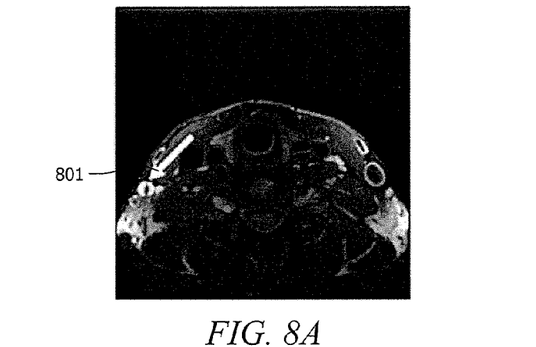
FIG. 8 illustrates the motion of a valve in a facial vein captured with a T2 weighted cineTSE reconstruction in accordance with an embodiment of the present application.
Figure 8B:
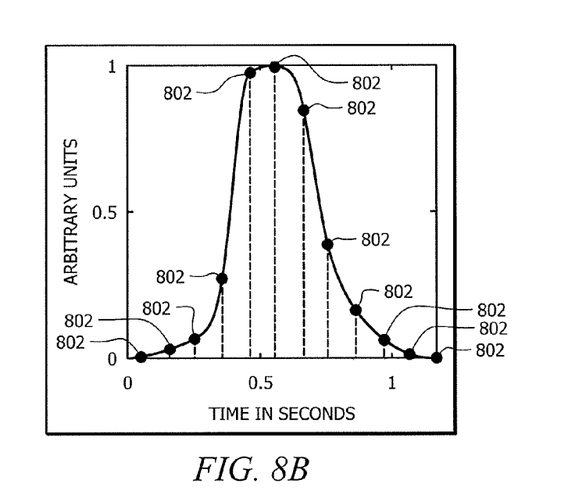
Figure 8C:
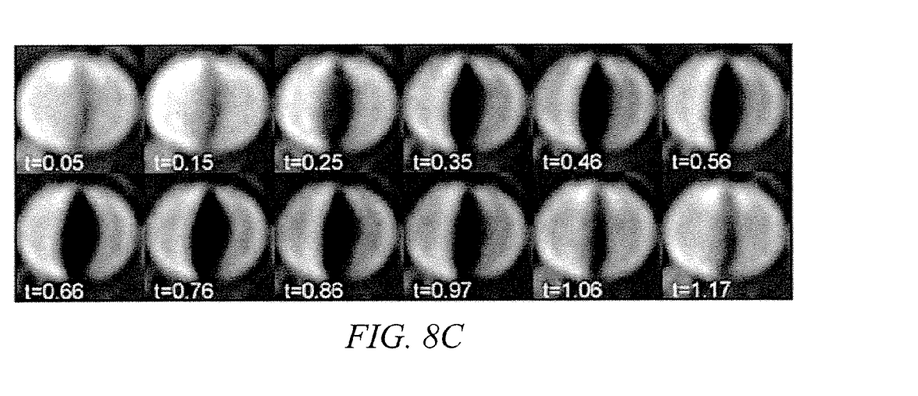

FIGS. 8A-C illustrate the motion of a valve 801 in a facial vein captured with a T2 weighted cineTSE reconstruction. FIG. 8A shows the standard TSE image with the average pressure waveform shown in FIG. 8B. Twelve cineTSE images of the valve indicated by arrow 801 at different times in the cardiac cycle are illustrated in FIG. 8C. The time of each image within the cardiac cycle is indicated by points 802 in FIG. 8B. Each of these times is taken with respect to the systolic trigger of the cardiac cycle. Where a typical TSE gated sequence returns images at one or two time points, it is noted that the cineTSE sequence delivers a whole set of images without an increase in scan time.

Figure 9A:
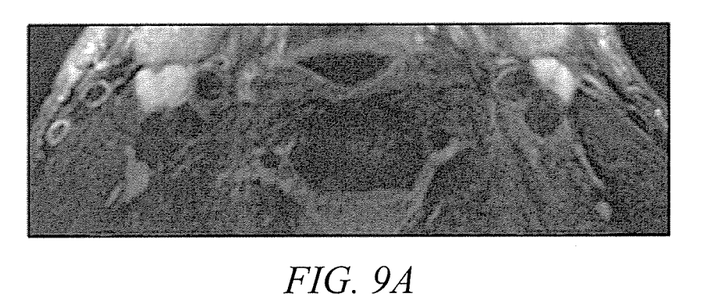
FIG. 9 illustrates example results from an embodiment to reduce a swallowing artifact.
Figure 9B:
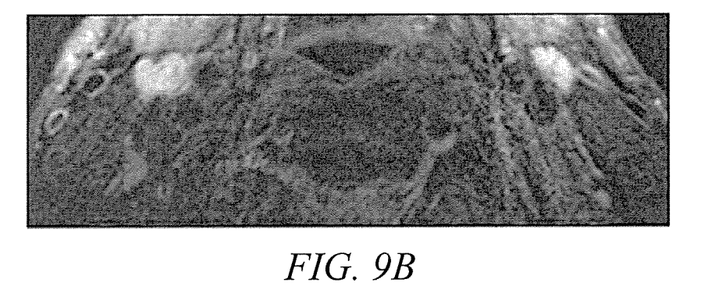
Figure 9C:
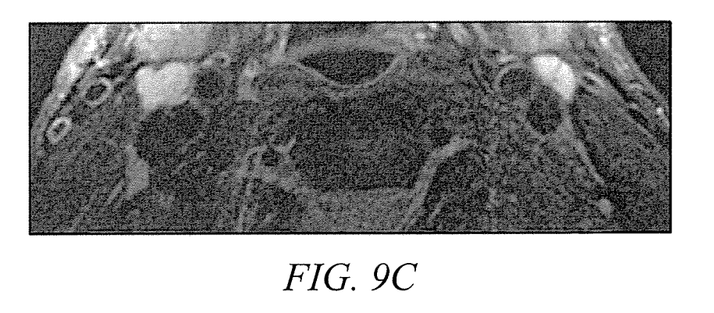

While the cineTSE technique is designed to eliminate cardiac related motion artifacts, other motion, such as swallowing, may still create artifacts. FIG. 9A illustrates an example where two averages in a standard TSE image can help to reduce a swallowing artifact. However, this method may eliminate some or all temporal cardiac information received since only a single time frame is reconstructed. When the corrupted data is sorted into multiple temporal bins (FIG. 9B), the swallowing artifact returns. The corrupted lines can be detected using data from adjacent data lines or from the same set of lines acquired in different averages. These lines can then be removed prior to the cineTSE reconstruction to reduce artifacts due to motion unrelated to the cardiac cycle (FIG. 9C).

Although ECG gating can reduce artifacts due to cardiac induced pulsations, gating is rarely used because it also lengthens the acquisition time, resulting in increased susceptibility to swallowing and respiratory motion artifacts. Many TSE protocols acquire two or more data averages to increase image signal to noise ratio and to help reduce the amount of motion artifact. One of the advantages of the cineTSE sequence is that it may be implemented with the same acquisition time of a standard two average TSE sequence. Examples shown in the present disclosure utilize the equivalent of two data averages. While a degree of temporal information could be obtained from just a single average of data, it is noted that in many cases at least two averages are used to yield consistent and accurate temporal information.

Another advantage of the cineTSE sequence is the ability to resolve certain flow artifacts and to discriminate between image signal from recirculating blood and tissue. This is evident in FIGS. 5A-C and 7A-D where residual blood signal may be misinterpreted for tissue wall. In the middle slice of FIGS. 7A-D, the systolic and diastolic images clearly show the ulceration, whereas the conventional image shows a lighter signal in the ulceration that might be interpreted as loose necrotic core. Additionally, it has been shown that in standard sequences pulsatile motion of vessels on the order of 1 mm peak to peak can occur, causing blurring of wall morphology. With a cineTSE sequence, it is possible to scroll through a dozen images at different time frames in the cardiac cycle and select the image(s) with least residual blood signal to best depict the vessel wall and plaque morphology. For example, FIG. 6A shows how using a systolic cineTSE image where fast moving blood gives no signal can be expected to more accurately depict vessel wall thickness compared to a standard TSE sequence.

T1 weighted images provide image contrast that is complementary to that of T2 weighted images and can therefore help discriminate plaque components. However, T1 weighted images have a short TE such that the signal from moving blood is not eliminated completely by the spin echo sequence. To eliminate the signal from moving blood, T1 weighted sequences may employ double inversion to eliminate the signal from flowing blood. However, double inversion techniques are very time-inefficient and require substantially longer acquisition times. Since cineTSE is able to distinguish flow artifacts, T1 weighted imaging may be performed without double inversion or other flow suppression techniques (FIGS. 7A-D). If it can be shown that blood signal can be detected and eliminated from analysis of T1 weighted images, then the cineTSE technique will substantially decrease the scan time typically required for standard T1 weighted TSE sequences. In this case, substantially more information will be obtained in less time.

In many cases, flow artifacts can be identified by selecting one or two images from the array of cineTSE images. However, since cineTSE produces images at several time points in the cardiac cycle, it is also well suited for applications that measure dynamic variables. FIG. 8 shows how cineTSE can capture the dynamic nature of a valve. Because motion of the carotid wall can be more clearly seen with cineTSE than with cine GRE sequences, it is likely that cineTSE coupled with systolic and diastolic pressures will provide a mechanism for measuring arterial wall compliance. Motion of the cerebrospinal fluid in the cervical spinal cord is also evident.

An additional advantage of a cineTSE sequence is that the data acquisition may be almost identical to a standard TSE sequence. As a result, many of the motion correction techniques (for non-cardiac related motion) developed for standard TSE sequences can be easily applied to the cineTSE sequence. Because many k-space lines have multiple averages, this data can be used to help detect corrupted data. Additionally, data from adjacent data lines can also be used to detect corruption from patient motion. Since undersampled data is already being obtained, it is not a significant problem if a few lines of data need to be discarded due to non-cardiac related motion corruption. As with many sequences, significant amounts of non-cardiac related motion may pose a problem. In FIG. 9, even though 20% of the data was discarded due to corruption, the cineTSE sequence produced images relatively free of cardiac motion artifact.

While this study focused on cineTSE of the neck, the sequence may be easily applied to other regions of the body, including the heart, where motion synchronized to the cardiac cycle is observed. Further, this technique could easily be adapted to other sequences, such as where a constant TR value and/or continuous scanning is required. Embodiments may also be adapted to perform with high resolution 3D sequences.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A magnetic resonance imaging system comprising:
   a transducer configured to generate raw turbo spin echo (TSE) magnetic resonance image data comprising a plurality of echo data acquisitions in response to an individual single RF excitation pulse;
   a monitoring device configured to generate motion data corresponding to periodic motion within a subject being imaged; and
   a processing device configured to receive the raw TSE image data and said motion data from said monitoring device, said processing device further configured to separate said raw TSE image data received across multiple periods of said periodic motion into respective bins comprising undersampled image representative data related to time divisions of a reference period of said periodic motion and to assign raw TSE image data of individual echo data acquisitions of said plurality of echo data acquisitions to said respective bins based on relative time of acquisition within a cardiac cycle, said processing device further configured to reconstruct the separated image data in accordance with said time divisions using said motion data to exclude raw TSE image data uncorrelated with a heart rate of said subject from use in the reconstruction.

2. The system of claim 1 wherein
said reconstruction generates a motion video image and
said processing device uses a bandpass filter selecting the frequency components in said raw TSE image data occurring near a frequency corresponding to a patient heart rate.

3. The system of claim 1 wherein
said processing device is further configured to utilize a parallel imaging technique to reconstruct said separated image data.

4. The system of claim 1 wherein said processing device is further configured to utilize a constrained reconstruction technique to reconstruct said separated image data.

5. The system of claim 1 wherein said transducer is configured to acquire TSE image data asynchronously with respect to said periodic motion.

6. The system of claim 1 wherein said respective bins are configured to temporally overlap and said processing device assigns raw TSE image data of an individual echo data acquisition of said plurality of echo data acquisitions to different overlapping bins to enable an overlapping data bin to include an adequate amount of data for reconstruction.

7. The system of claim 1 wherein said processing device is further configured to average multiple raw TSE image data separated into a respective bin for image reconstruction.

8. The system of claim 1 wherein said processing device is configured to eliminate motion artifacts of said images caused by a cardiac cycle.

9. The system of claim 1 wherein said processing device is configured to identify flow artifacts in image data corresponding to recirculating blood during image reconstruction.

10. A magnetic resonance imaging method comprising the activities of:
employing a transducer to generate raw turbo spin echo (TSE) magnetic resonance image data comprising a plurality of echo data acquisitions generated in response to an individual single RF excitation pulse;
generating motion data corresponding to periodic motion within a subject being imaged;
receiving the raw TSE image data and said motion data;
separating said raw TSE image data received across multiple periods of said periodic motion into respective bins comprising undersampled image representative data related to time divisions of a reference period of said periodic motion by assigning raw TSE image data of individual echo data acquisitions of said plurality of echo data acquisitions to said respective bins based on relative time of acquisition within a cardiac cycle; and
reconstructing the separated image data in accordance with said time divisions by using said motion data to exclude raw TSE image data uncorrelated with a heart rate of said subject from use in the reconstruction.

11. The method of claim 10 wherein
said reconstruction generates a motion video image and including the activity of
using a bandpass filter selecting the frequency components in said raw TSE image data occurring near a frequency corresponding to a patient heart rate.

* * * * *